(12) United States Patent
Marshall et al.

(10) Patent No.: US 9,579,460 B2
(45) Date of Patent: Feb. 28, 2017

(54) INJECTION DEVICES

(75) Inventors: Jeremy Marshall, Oxford (GB); Toby Cowe, Oxford (GB)

(73) Assignee: OWEN MUMFORD LIMITED, Oxford (GB)

( * ) Notice: Subject to any disclaimer, the term of this patent is extended or adjusted under 35 U.S.C. 154(b) by 331 days.

(21) Appl. No.: 14/117,087

(22) PCT Filed: May 11, 2012

(86) PCT No.: PCT/GB2012/051062
§ 371 (c)(1),
(2), (4) Date: Apr. 9, 2014

(87) PCT Pub. No.: WO2012/153150
PCT Pub. Date: Nov. 15, 2012

(65) Prior Publication Data
US 2014/0236076 A1  Aug. 21, 2014

Related U.S. Application Data

(60) Provisional application No. 61/485,451, filed on May 12, 2011.

(30) Foreign Application Priority Data

May 12, 2011 (GB) .................................. 1107943.1

(51) Int. Cl.
  *A61M 5/20* (2006.01)
(52) U.S. Cl.
  CPC ............ *A61M 5/20* (2013.01); *A61M 5/2033* (2013.01); *A61M 2005/206* (2013.01);
(Continued)

(58) Field of Classification Search
CPC .... A61M 5/16836; A61M 5/44; A61M 5/445; A61M 5/50; A61M 5/24;
(Continued)

(56) References Cited

U.S. PATENT DOCUMENTS 3,713,067 A * 1/1973 Gressenich ............ H01H 37/52
  337/112
6,241,709 B1 6/2001 Bechtold et al.
(Continued)

FOREIGN PATENT DOCUMENTS

CN 1419458 5/2003
CN 1942208 4/2007
(Continued)

OTHER PUBLICATIONS

International Search Report, dated Aug. 1, 2012, from corresponding PCT application.
(Continued)

*Primary Examiner* — Aarti B Berdichevsky
(74) *Attorney, Agent, or Firm* — Young & Thompson

(57) ABSTRACT

An injection device operable to deliver a dose of medicament from a syringe or cartridge includes a temperature-sensitive arrangement for inhibiting operation thereof under predetermined temperature conditions. This may include a thermally responsive element that adopts a position in which operation of the device is inhibited when a temperature level is passed.

3 Claims, 2 Drawing Sheets

(52) U.S. Cl.
CPC ............... *A61M 2205/0227* (2013.01); *A61M 2205/0266* (2013.01); *A61M 2205/0272* (2013.01)

(58) Field of Classification Search
CPC .. A61M 2005/2073; A61M 2005/3125; A61M 2205/3368; A61M 5/20; A61M 5/2033
USPC ................ 604/31, 65, 66, 67, 218, 232, 503
See application file for complete search history.

(56) References Cited

U.S. PATENT DOCUMENTS

| | | | |
|---|---|---|---|
| 6,682,504 | B2 | 1/2004 | Nelson et al. |
| 7,678,072 | B2 | 3/2010 | Weber |
| 2007/0270777 | A1 | 11/2007 | Dacquay et al. |
| 2008/0097311 | A1* | 4/2008 | Dacquay ............... A61F 9/0017 604/113 |
| 2008/0287785 | A1 | 11/2008 | Saitoh et al. |
| 2009/0036868 | A1* | 2/2009 | Pinedjian ............... A61F 9/0017 604/506 |

FOREIGN PATENT DOCUMENTS

| | | | | |
|---|---|---|---|---|
| CN | | 101267856 A | 9/2008 | |
| EP | | 2130561 A1 | 12/2009 | |
| GB | | 2477046 | 7/2011 | |
| WO | | 02/28458 A1 | 4/2002 | |
| WO | | 2005/072794 A2 | 8/2005 | |
| WO | | 2008/108887 A2 | 9/2008 | |
| WO | | 2008/146021 A1 | 12/2008 | |
| WO | WO 2008/146021 A1 * | | 12/2008 | ............ A61M 5/44 |
| WO | | 2009/007951 A2 | 1/2009 | |
| WO | | 2009/022132 A2 | 2/2009 | |
| WO | | 2010-056712 | 5/2010 | |
| WO | | 2010127449 A1 | 11/2010 | |
| WO | | 2011-067268 | 6/2011 | |

OTHER PUBLICATIONS

GB Search Report, dated Aug. 31, 2011, from corresponding GB application.
Chinese Office Action, dated Dec. 2, 2014, from corresponding CN application.
GB search report, dated Jan. 27, 2016; Application No. 1107943.1.
CN Office Action, dated Oct. 8, 2015; Application No. 201280022994.6.

* cited by examiner

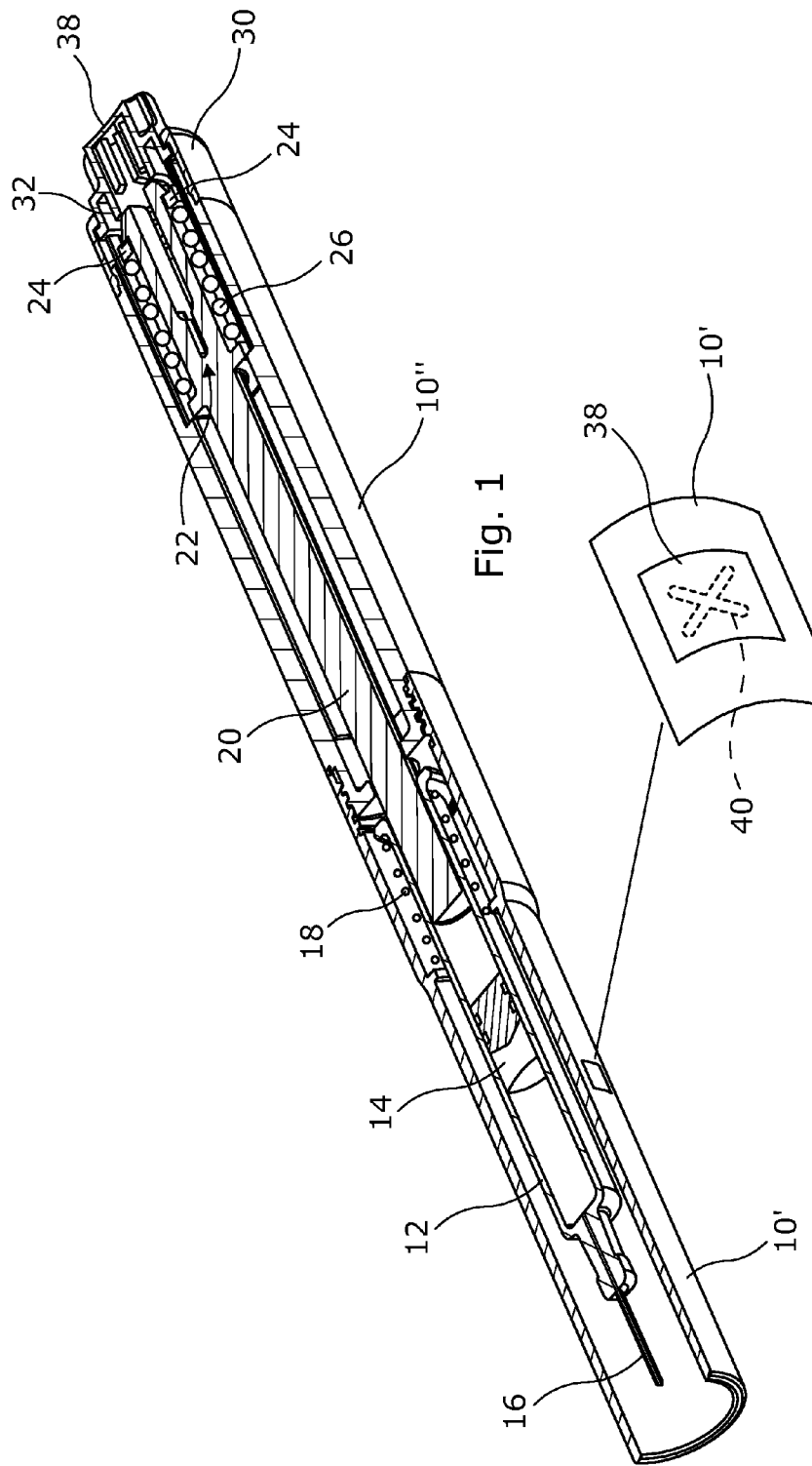

INJECTION DEVICES

BACKGROUND OF THE INVENTION

This invention relates to injection devices and in particular but not exclusively to autoinjectors in which all or part of the injection cycle is automated. The invention also relates to syringes and other hand-operated injection devices.

It is generally desirable that an autoinjector performs consistently over a wide temperature range. Although this is achievable in some cases, in others, particularly where the fluid or material properties of the substance or substances to be injected vary significantly with temperature, it may not be possible to provide an autoinjector device that performs consistently at very low or very high temperatures or outside a given temperature range. For example the viscosity of a medicament may vary quite significantly with temperature.

Accordingly we have designed an injection device in which the user is alerted if the temperature of the autoinjector is not consistent with the operating range of temperatures. This alert may be active, by inhibiting operation of the device, or passive, by providing a visual indicator, or a combination of both.

BRIEF SUMMARY OF THE INVENTION

Accordingly, in one aspect this invention provides an injector device operable to deliver a dose of medicament from a syringe or cartridge and including a temperature-sensitive arrangement for inhibiting operation thereof under predetermined temperature conditions.

In this way the user may be prevented from using the device under adverse temperature conditions.

Operation may be inhibited for example, when a detected temperature is below a predetermined threshold temperature, or when a detected temperature is above a predetermined threshold temperature, or when a detected temperature is outside a predetermined range.

Conveniently the autoinjector includes a drive mechanism releasable to express a dose from a syringe or cartridge contained within a housing, and which may additionally be operable to move said syringe or cartridge relative to said housing to cause a needle at a forward end of said syringe or cartridge to project from said housing to penetrate an injection site in use, prior to expressing said dose. In this case, said drive mechanism may include a plunger releasable from a cocked position to move forwardly under the influence of a drive spring, and said temperature-sensitive arrangement may inhibit release of said drive mechanism. Release may be inhibited by blocking movement of a firing element, or by preventing unlatching of a latch arrangement retaining the plunger in its cocked position.

Typically existing autoinjectors require two or more operations to be performed to fire the device. For example, a firing trigger may only be movable to a fired position if a safety sleeve has been shifted relative to the device when the device is pressed against an injection site, or after release of a safety catch. In embodiments of this invention the thermally responsive member may directly inhibit movement of the firing trigger, or it may inhibit movement of a safety catch or the like which must be moved to allow the firing trigger to become live.

Advantageously said temperature-sensitive arrangement includes a thermally responsive member which, upon passing a predetermined temperature adopts a position in which it inhibits operation of said autoinjector. This may be an upper or lower limit temperature.

The position of the thermally responsive member may vary continuously with temperature, or the thermally responsive member may undergo a discrete movement at a predetermined temperature.

Conveniently two thermally responsive members are provided, one being designed to inhibit operation of the device below a first predetermined temperature and the other being designed to inhibit operation of the device above a second predetermined temperature.

The or each thermally responsive member may be any suitable member that changes shape with temperature, such as is a bi-morph or bi-metallic strip, or a shape memory alloy element.

In another embodiment said temperature-sensitive arrangement may include an electrically driven inhibiting element responsive to the output of a heat sensor to inhibit operation of said autoinjector.

In addition to actively inhibiting operation, the autoinjector may include an externally visible heat-sensitive indicator operable to provide a visual indication under predetermined temperature conditions. For example said heat-sensitive indicator may undergo a change in colour under predetermined temperature conditions. Alternatively, said heat-sensitive indicator may comprise a coating of thermochromic material adapted to reveal or conceal a symbol or indicia relating to the operational state of the autoinjector under predetermined temperature conditions.

In another aspect, this invention provides an injector device including an externally visible heat-sensitive indicator operable to provide a visual indication of the operational state of the device, under predetermined temperature conditions.

Whilst the invention has been described above it extends to any inventive combination of the features set out above or in the following description, claims or drawings.

BRIEF DESCRIPTION OF THE DRAWINGS

The invention may be performed in various ways, and, an embodiment thereof will now be described by way of example only, reference being made to the accompanying drawings in which:

FIG. 1 is a horizontal section view through an embodiment of autoinjector in accordance with this invention;

FIG. 2 is a detailed view on a portion of the barrel thereof;

DETAILED DESCRIPTION OF THE PREFERRED EMBODIMENTS

Figure 3:
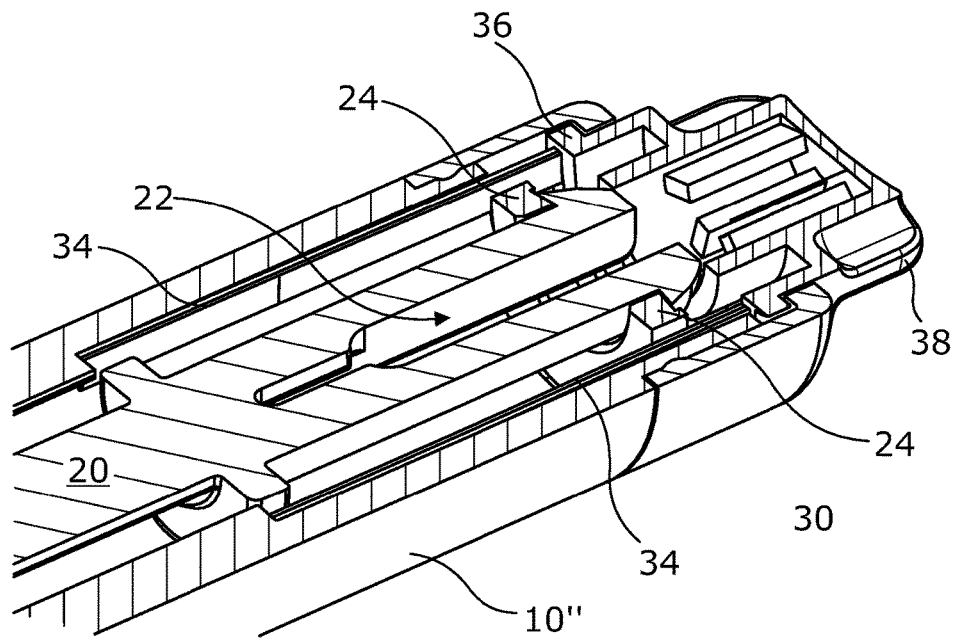
FIG. 3 is a detailed on the rear end showing forward movement of the trigger button inhibited by a heat sensitive element.

The autoinjector shown in the drawing comprises a two part housing comprising forward and rearward generally cylindrical housing parts 10',10" connected by a screw coupling. A syringe 12 having a piston 14 and a needle 16 is mounted in the forward housing part 10' for movement against the bias of a spring 18 between the retracted position shown in FIG. 1 in which the needle is inside the forward housing 10', and an extended position in which the needle 16 projects therefrom.

The rear housing part 10" contains an elongate plunger 20 having a forward end which fits inside the barrel of the syringe 12 and a rear end having a split arrowhead formation 22 that engages behind a fixed shoulder 24 in the rear end of the rear housing part 10". The plunger 20 is biased forwardly by a main drive spring 26. A firing button 28 is retained on the rear end of the housing 10',10" by means of a collar 30. The firing button 28 has an inner shell 32 that, when the button 28 is pushed forwardly, squeezes together the split arrowhead 22 so that it is released from the shoulder 24 allowing the plunger to move forwardly under the influence of the main drive spring 26. A safety interlock may be provided which requires relative rotation of one or more of the trigger button 28, the collar 30 and the rear housing part 10".

On firing the device, the plunger 20 moves forwardly to contact the piston 14 and initially to move the syringe forward in the housing until it reaches it forwardmost position, with the needle 16 extending forwardly from the device to penetrate the injection site. Thereafter continued expansion of the spring moves the piston 14 down the syringe to deliver a dose.

Figure 4:
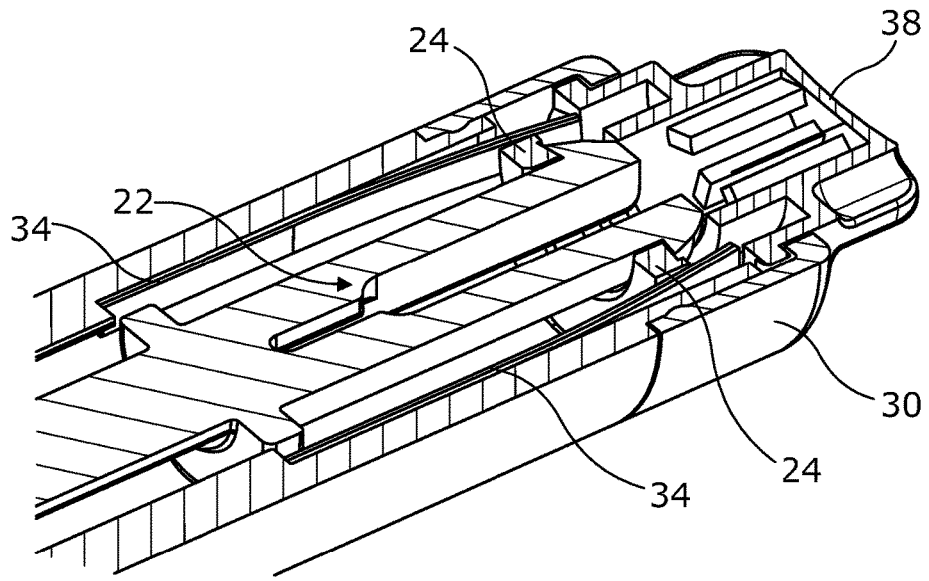
FIG. 4 is a similar view but showing the heat sensitive element shifted to allow forward movement of the trigger button.

The autoinjector device is specially designed to include a temperature sensitive arrangement for inhibiting operation of the device if the temperature is less than a predetermined threshold. The temperature sensitive arrangement includes two diametrically opposed bimetallic strips 34 that are anchored at their forward ends to the inner wall of the rear housing part 10" in cantilever fashion so that they can flex inwardly as the temperature increases. In the low temperature position (FIG. 3) the bimetallic strips 34 bear against the inner wall of the housing part 10',10" and align with a forward flange 36 of the plunger button 38 so that the button is prevented from forward movement and so the device cannot be fired. However, when the temperature experienced by the bimetallic strips increases to a level above a predetermined temperature threshold, the bimetallic strips 34 flex inwardly to the position shown in FIG. 4 where they no longer obstruct the forward flange 36 and so the trigger button 38 can be depressed to fire the device.

The bimetallic strips are just one way of achieving this function. Other "smart metals" or temperature sensitive shape memory alloys may instead be used which likewise undergo a change of shape at or beyond a predetermined temperature. Furthermore, a further set of temperature sensitive strips may be provided which alter shape to block forward movement of the firing button 28 when their temperature exceeds a particular threshold temperature but otherwise permit forward movement of the button. These may be spaced at 90° to the pair of lower limit strips. In this manner operation of the device is inhibited when it is outside a predetermined range of temperatures.

Referring again to FIG. 1, the forward housing part 10' includes a thermally sensitive indicator region 38 which changes state when a particular operating temperature limit is passed. In a particular embodiment, the thermally sensitive region comprises a coating of thermochromic material. The coating may for example be selected so that it undergoes a colour change at a relevant threshold temperature. Alternatively, the coating may change state from clear to opaque or vice versa at a particular temperature change, thereby revealing or concealing a suitable symbol 40 or the like. Again, the indication may change from clear to opaque or vice versa when the temperature moves outside a particular range. The selection and design of suitable such thermochromic materials will be well known to those skilled in the art.

Although heat sensitive elements that change position and/or shape continuously with temperature or at discrete transition temperatures are preferred, in yet another embodiment, not illustrated, a temperature sensor may be provided in or on the housing, and an electrically operated latch or the like may be moved to permit/prevent firing of the device dependant on the temperature detected by the sensor.

The invention claimed is:

1. An injection device operable to deliver a dose of medicament from a syringe having a barrel, a piston, and a needle, the injection device comprising:
    a housing comprising a forward part (10') and a rearward part (10"), the syringe housed in the housing, the syringe movable between i) a retracted position in which the needle is entirely inside the forward part of the housing and ii) an extended position in which the needle projects from the forward part of the housing;
    a drive mechanism located in the rearward part of the housing and including a drive spring (26) and an elongate plunger (20) movable, under influence of the drive spring (26), forward from i) a retained initial position, to ii) a released final position, the elongate plunger moving from the retained initial position, to the released final position acting against the piston of the syringe to express the dose from the syringe contained within the housing;
    a firing element (28) retained in the housing in an initial position, the elongate plunger being retained in the initial position while the firing element is retained in the initial position, the firing element being movable from the initial position to fire the injection device, the firing element moving from the initial position releasing the elongate plunger from the retained initial position, thereby allowing the elongate plunger, under the influence of the drive spring, to move forward from the retained initial position to the released final position to thereby express the dose from the syringe; and
    a temperature-sensitive arrangement that includes a thermally responsive element, the thermally responsive element having i) a first blocking position that blocks movement of the firing element from the initial position and prevents firing of the injection device, to ii) and a second non-blocking position that does not block movement of the firing element from the initial position and allows firing of the injection device, wherein the thermally responsive element remains in the first blocking position under a predetermined temperature condition, wherein,
    the thermally responsive element includes a pair of diametrically opposed bi-metallic strips anchored to the inner wall of the housing and cantilevered from the inner wall of the housing,
    in the first blocking position, the bi-metallic strips are flexed outwardly adjacent the inner wall of the housing with a distal end of each of the bi-metallic strips being in the first blocking position that blocks the movement of the firing element from the initial position, and
    in the second non-blocking position, the bi-metallic strips are flexed inwardly away from the inner wall of the housing with the distal end of each of the bi-metallic strips being in the second non-blocking position that does not block movement of the firing element from the initial position.

2. The injection device of claim 1, wherein said predetermined temperature condition is a predetermined first threshold temperature, and the thermally responsive element undergoes a discrete movement to adopt the first blocking position when the temperature changes from an initial temperature above the predetermined first threshold temperature to a current temperature below the predetermined first threshold temperature.

3. The injection device of claim 2, wherein said predetermined temperature condition further includes a predetermined second threshold temperature, and the thermally responsive element undergoes another discrete movement to adopt the first blocking position when the initial temperature changes to be above the predetermined second threshold temperature.

\* \* \* \* \*